United States Patent [19]

Saischek et al.

[11] 4,265,664
[45] May 5, 1981

[54] SPIROCYCLIC BORON COMPOUNDS, A PROCESS FOR THEIR MANUFACTURE AND THEIR USE AS A FLAME-RETARDANT ADDITIVE

[75] Inventors: Gerald Saischek, Wels; Karlheinz Wegleitner, Linz; Ferdinand Heu, Linz; Roman Wohlmuth, Linz, all of Austria

[73] Assignee: Chemie Linz Aktiengesellschaft, Linz, Austria

[21] Appl. No.: 38,300

[22] Filed: May 11, 1979

[30] Foreign Application Priority Data

May 12, 1978 [DE] Fed. Rep. of Germany ....... 2820909

[51] Int. Cl.³ .................................................. C07F 5/04
[52] U.S. Cl. .................................. 106/18.13; 106/18.21; 106/18.25; 260/429 R; 260/429.9; 260/432; 260/462 R
[58] Field of Search ............ 260/462 R, 429.9, 429 R, 260/432; 106/18.21, 18.25, 18.13

[56] References Cited

U.S. PATENT DOCUMENTS

| | | | |
|---|---|---|---|
| 2,497,521 | 2/1950 | Trautman | 252/389 |
| 3,035,887 | 5/1962 | Willcockson | 260/462 R |
| 3,221,035 | 11/1965 | Silver | 260/462 R X |
| 3,373,170 | 3/1968 | Jones | 260/462 R X |
| 3,403,304 | 9/1968 | Ross et al. | 260/462 R X |
| 3,403,305 | 9/1968 | Santway et al. | 260/462 R X |
| 3,539,614 | 11/1970 | Ross et al. | 260/462 R |
| 3,544,614 | 12/1970 | Schwartz | 260/462 R |
| 3,635,848 | 1/1972 | Rambosek | 260/2.5 AB |
| 3,639,234 | 1/1972 | Wixon | 260/462 R X |
| 3,772,357 | 11/1973 | Hamanaka | 260/462 R X |
| 4,021,464 | 5/1977 | Mayerhoefer et al. | 260/462 R |

FOREIGN PATENT DOCUMENTS

1402766  8/1975  United Kingdom ................ 260/462 R

*Primary Examiner*—Helen M. S. Sneed
*Attorney, Agent, or Firm*—Wenderoth, Lind & Ponack

[57] ABSTRACT

Novel spirocyclic boron compounds of the formula

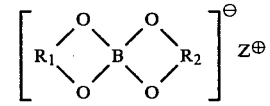

in which $R_1$ and $R_2$ are various halogen containing organic radicals and $Z+$ is a hydrogen ion, an equivalent of an alkaline-earth metal ion, a guanidinium ion or alkylammonium ion as flame retarding agents in various plastics, such as polyurethanes, epoxide resins and polyesters.

16 Claims, No Drawings

SPIROCYCLIC BORON COMPOUNDS, A PROCESS FOR THEIR MANUFACTURE AND THEIR USE AS A FLAME-RETARDANT ADDITIVE

The invention relates to spirocyclic boron compounds, their manufacture and their use as a flame-retardant additive for various plastics, such as polyurethanes, epoxide resins and polyesters.

It is known that most plastics which are usually flammable, such as polyolefines, polystyrene, polymethacrylates, polyvinyl acetate, polyvinyl acetals, polyamides, polyesters, polyurethanes, polycarbonates and epoxide resins, can be rendered more difficult to ignite or even nonflammable by additions of certain chemical compounds. Such chemical compounds usually contain phosphorus, nitrogen and halogen, such as chlorine or, in particular, bromine, and flame-retardant action being further intensified by additions of compounds of main group 5 of the periodic system, such as antimony compounds or bismuth compounds, in particular antimony trioxide.

Thus, for example, polyurethane foams can be provided with a flameproof finish by adding halogenated phosphoric acid esters. (M. W. RANNEY "Fire resistant and flame retardant polymers" pages 90 to 92). However, if these flame-retardant substances are admixed with polyurethane foam batches which contain, in addition to the diisocyanate component, all the additives necessary for foaming, these mixtures exhibit a certain instability. This instability arises from the fact that the halogen in these phosphorus compounds can be split off more of less readily, especially by traces of water, and the tertiary amines added to the mixture are thereby deactivated as a result of salt formation.

Another possibility for the manufacture of flameproof polymers consists of a process in which a brominated monomer is added during the polymerization or polycondensation of a plastic and is thereby incorporated directly into the molecular structure. An example of this would be the manufacture of an epoxide resin, one component of which is bisphenol A. To manufacture a flameproof epoxide resin, tetrabromobisphenol A is co-condensed. The high amounts added of 30 to 33% by weight, which are required in this procedure, prove to be a disadvantage since considerable changes in the properties of the epoxide resin can already be established (German Offenlegungsschrift No. 2,503,368).

The reaction of boric acid or boric acid derivatives with organic, halogen-containing hydroxy compounds to give boric acid esters, which are particularly suitable as flameproof additives to polypropylene, which is then melt-spun, or also for impregnating polypropylene fabric, is described in British Patent Specification No. 1,402,766.

Spiro-boron compounds, that is to say compounds in which the boron is tetravalent, are likewise already known, not for the purpose of flame-retarding but as an oil additive or as a catalyst for the manufacture of polyurethanes, polyisocyanurates or isocyanurates.

Thus, for example, in U.S. Pat. Specification No. 2,497,521, a boric acid-ethylene glycol complex compound is manufactured, by heating boric acid and ethylene glycol, and isolated and, after heating with an amine, gives the corresponding amine salt of the spiro-boron compound. Boric acid and ethylene glycol are employed in a 30% excess. A number of compounds which increase the storability and resistance to corrosion of oils based on hydrocarbons have been manufactured in this manner. In U.S. Patent Specification No. 3,635,848, Na salts of spiro-boric acid esters are described which were manufactured by heating boric acid with a large excess of a glycol, the water formed being distilled off in vacuo, and then heating the reaction product with metallic sodium. These compounds are suitable as catalysts for the manufacture of polyurethanes and polyisocyanurates, for the trimerization of isocyanates and the like.

In contrast, a new class of spirocyclic, halogen-containing boron compounds has now been found, which has outstanding flame-retardant properties and a good chemical stability. These spiro-boron compounds are manufactured by heating equivalent amounts of boric acid or boron trioxide with a halogen-containing dihydroxy compound and a strong base.

The present invention accordingly relates to spirocyclic boron compounds of the general formula

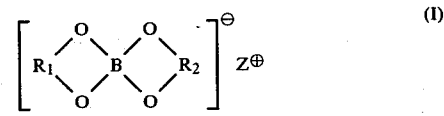

wherein $R_1$ and $R_2$, which may be the same or different each are dihalogeno alkylene, having 2 to 6 carbon atoms, a halogen-substituted bis-methyleno-bicycloheptene-radical, tetrahalogeno-o,o'-phenylene, tetrachloro-o,o'-biphenylene, tetrabromo-o,o'-biphenylene or a group of the formula

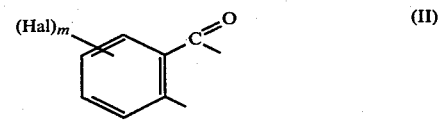

in which Hal is chlorine or bromine and m is the integer 3 or 4, and $Z^+$ is hydrogen ion, alkali metal ion, an equivalent of a divalent ion of a metal of group 2 of the periodic system, a guanidinium or hydrazinium ion or an ion of the formula

wherein $R_3$, $R_4$, $R_5$ and $R_6$, which may be the same or different each are hydrogen, alkyl with 1 to 8 carbon atoms, cycloalkyl with 5 or 6 carbon atoms or phenyl, whereby in the case where one of the radicals $R_3$, $R_4$, $R_5$ and $R_6$ is phenyl, the other ones have a meaning other than phenyl.

Preferred compounds are spirocyclic boron compounds of formula I above, which derive from aliphatic alcohols having 4 or 5 carbon atoms, per example from 1,4-dihydroxy-2,3-dibromo-ethane, 1,4-dihydroxy-2,3-dichloro-ethane, 1,3-dihydroxy-2,2-bis-chloromethyl-, -bis-bromomethyl- or -bis-iodomethyl-propane. Other preferred compounds are the spirocyclic boron compounds of formula I which derive from tetrabromopyrocatechol or from tetrabromo-biphenol, from tetrabromosalicyclic acid or from hexachlorobishydroxymethylbicycloheptene.

The new compounds of the formula I are manufactured by a procedure in which 1 mol of boric acid or boron trioxide is reacted with one or, if $R_1$ is identical to $R_2$, with two mols of a diol of the general formula

$$R_1 \begin{matrix} \diagup OH \\ \diagdown OH \end{matrix} \qquad (III)$$

in which $R_1$ has the meaning indicated above, and, if $R_1$ is different from $R_2$, then with one mol of a diol of the general formula

$$R_2 \begin{matrix} \diagup OH \\ \diagdown OH \end{matrix} \qquad (IV)$$

in which $R_2$ has the meaning indicated above, in the presence of at least 1 mol of a base or of a salt, having a basic reaction, of the formula $Z^+Y^-$, wherein $Z^+$ is as defined above and $Y^-$ denotes an OH ion or the ion of a weak acid, at a temperature from 20° to 200° C., preferably at a temperature from 60° to 150° C., in an inert solvent. Examples of such bases or salts having a basic reaction are: guanidine carbonate, tetraalkylammonium hydroxide, tri-, di- or monoalkylammonium hydroxides, cyclohexylammonium hydroxide, ammonium hydroxide, hydrazinium hydroxide, alkali metal hydroxides or alkaline earth metal hydroxides or carbonates. Preferred bases are guanidine carbonate, triethylamine, diethylamine and sodium carbonate.

Possible halogen-containing dihydroxy compounds are, above all, pyrocatechol derivatives which are tetrasubstituted by bromine, as well as derivatives of $\alpha,\alpha'$-dihydroxydiphenyl or of ethylene glycol, propylene glycol, butylene glycol, neopentylglycol, hexanediol or bicycloheptenedimethylol, and derivatives of salicyclic acid which are trisubstituted or tetrasubstituted by Cl or Br. These compounds are known and can be manufactured by one of the processes described in the literature, that is to say by the addition of halogen onto a double bond or by replacement of hydrogen atoms by halogen.

The reactions can be carried out under atmospheric pressure or under increased or reduced pressure. The reaction temperatures can also vary within wide limits. The reaction is advantageously carried out at a temperature from 20° to 200° C., preferably between 60° and 150° C. The reaction can advantageously be carried out in a water-immiscible solvent, such as toluene, xylene or chloroform. The water of reaction formed in the condensation reaction between boric acid or boron trioxide and the dihydroxy compound is thereby distilled off from the reaction mixture azeotropically.

However, it is also possible to carry out the reaction without removal of the water of reaction, in a watermiscible liquid, such as, for example, methanol, or directly with water or in a mixture of the two. When the reaction has ended, in most cases a crystalline, colorless solid which can be filtered off, dried and if necessary recrystallized is obtained in high yields.

The new compounds of the formula I are outstandingly suitable as flame-retardant agents and can be added to numerous polymers. The amounts thereby used depend on the particular chemical composition of the polymer and on its physical state. Amounts of 1 to 25% by weight are usually required, it being possible to intensify the flame-retardant action further by adding a synergistic agent. Such synergistic agents are known; they are oxides or halides of bismuth, arsenic or antimony. Antimony oxides are the preferred synergistic agents. These synergistic agents are added in amounts of 1 to 15% by weight, relative to the weight of the plastic provided with the finish, and 25 to 75% by weight, relative to the weight of the particular flame-retardant used. In addition, other fillers, such as aluminum hydroxide, which assist the action of the flame-retardant substances can also be admixed.

The compounds of the formula I are particularly suitable as flameproofing agents for polyurethanes, since they are very stable chemically, are readily soluble in organic solvents, in warm polyol and in other organic solvents and are distinguished by a good stability on storage.

The amount of compounds of the formula I added depends on the extent of the flame-retardant action required for the particular intended use of the finished plastic. In general, amounts of 8 to 25 parts of a compound of the formula I per 100 parts of polyol are sufficient to render polyurethanes self-extinguishing or non-flammable according to ASTM Test D 1692-67T, depending on whether synergistic agents have been added, and in what amount. Table 1 demonstrates the possibilities regarding the values which can be obtained with regard to the extent of burning, the burning rate and the classification into self-extinguishing and non-flammable according to ASTM Test D 1692-67T.

It is found that, as expected, without the addition of a synergistic agent, higher amounts of a compound of the formula I are necessary to achieve self-extinguishing properties. By appropriate variation of the amounts of compound of the formula I and synergistic agent employed, it is even possible to achieve extents of burning of only 1.81 cm and thus a burning rate of only 1.96 cm/minute according to ASTM Test D 1692-67T.

The compounds of the formula I described also prove to be particularly effective in epoxide resins. Thus, as can be seen from Table 2, with the compound according to Example 1, the self-extinguishing class according to ASTM Test 635-63 can already be achieved with an amount added of 10% by weight and without the addition of a synergistic agent. With 15% by weight of the compound according to Example 11 and an addition of 2.5% by weight of $Sb_2O_3$, the resin becomes non-burning.

Polyester resins thus already become non-flammable with a few percent of the compounds of the formula I.

Several examples for the manufacture of the compounds of the formula I and their use for the manufacture of flameproof plastics are described in the following text. However, the examples indicated are in no way intended to limit the extent of the invention.

EXAMPLE 1

212.8 parts of tetrabromopyrocatechol in a mixture consisting of 586 parts of methanol and 147.26 parts of a 25% strength by weight methanolic tetraethylammonium hydroxide solution are brought to the reflux temperature in a stirred apparatus with reflux cooling. On heating the mixture, the tetrabromopyrocatechol dissolves completely. A hot solution consisting of 100 parts of water and 15.45 parts of boric acid is now added to this solution at the reflux temperature in one operation. After some minutes, the reaction product starts to precipitate. The solution is kept at the reflux temperature for a further 1 hour. The solution is then cooled and the reaction product is filtered off. 224.87 parts of tetraethylammonium bis-(tetrabromopyrocatecholato)-borate(1-) are obtained;
melting point=278°-280° C.

EXAMPLE 2

106.25 parts of tetrabromopyrocatechol, 12.5 g of triethylamine and 7.7 parts of boric acid in 400 ml of toluene are brought to the reflux temperature in a stirred apparatus provided with a water separator. After some minutes, complete solution of the components occurs. 6.7 parts of $H_2O$ are separated off with the aid of the water separator. The solution is kept at the reflux temperature for a further 1 hour. After cooling the solution, the product is then filtered off. 109.2 g of triethylammonium bis-(tetrabromopyrocatecholato)-borate(1-) are obtained;
melting point=>250° C. (decomposition).

EXAMPLE 3

9.08 parts of tetrabromosalicyclic acid, 0.62 part of boric acid and 3.8 parts of a 24% strength methanolic tetramethylammonium hydroxide solution in 90 ml of $H_2O$ and 50 ml of methanol are made up into a suspension in a stirred apparatus. The mixture is kept at the reflux temperature for 3 hours. The mixture is then cooled and the reaction product is filtered off. 9.2 parts of tetramethylammonium bis-(tetrabromosalicylato)-borate(1-) are obtained;
melting point=>268° C. (decomposition).

EXAMPLE 4

17.6 parts of sodium bis-(tetrabromopyrocatecholato)borate(1-) are dissolved in 180 ml of ethanol in a stirred apparatus. 1.36 parts of zinc chloride are added to this solution. The solution is kept at the reflux temperature for 1 hour. 100 ml of ethanol are then removed by distillation and the residue is stirred into 1,500 parts of water. After filtering off the voluminous, white precipitate, 14 parts of zinc bis-[bis-(tetrabromopyrocatecholato)-borate(1-)]pentahydrate are obtained;
melting point=179°-183° C. (decomposition).

EXAMPLE 5

78.5 parts of 2,2-bis-(bromomethyl)-propane-1,3-diol and 9.3 parts of boric acid are suspended in 100 ml of water in a stirred apparatus and the suspension is kept at 90° C. for 1 hour, whilst stirring. 8.4 parts of KOH are then added slowly. The solution is concentrated and 61 parts of potassium bis-[2,2-bis-(bromomethyl)-propane-1,3-diolato]borate(1-) are obtained;
melting point=>215° C. (decomposition).

The following compounds were prepared analogously:

EXAMPLE 6

Tetraethylammonium bis[(3,3',5,5'-tetrabromo-1,4'-biphenyl)-2,2'-diolato-O,O']-borate(1-);
melting point=251°-255° C.

EXAMPLE 7

Guanidine bis-[(3,3',5,5'-tetrabromo-1,1'-biphenyl)2,2'-diolato-O,O']-borate(1-);
melting point=>400° C. (decomposition).

EXAMPLE 8

Ammonium bis-(tetrabromopyrocatecholato)-borate(1-);
melting point=>298° C. (decomposition).

EXAMPLE 9

Sodium bis-(tetrabromopyrocatecholato)-borate(1-);
melting point=>350° C. (decomposition).

EXAMPLE 10

Guanidine bis-(2,3-dibromo-1,4-butanediolato)-borate(1-);
melting point=142°-145° C.

EXAMPLE 11

Guanidine bis-[2,2-bis-(bromomethyl)-1,3-propanediolato]-borate(1-);
melting point=218°-223° C.

EXAMPLE 12

Sodium bis-[2,2-bis-(bromomethyl)-1,3-propanediolato]-borate(1-);
melting point=192°-194° C.

EXAMPLE 13

Tetramethylammonium bis-(tetrabromosalicylato)-borate(1-);
melting point=268° C. (decomposition).

EXAMPLE 14

Guanidine bis-[2,2-bis-iodomethyl)-1,3-propanediolato]-borate(1-);
melting point=220°-222° C.

EXAMPLE 15

Potassium bis-[(3,3',5,5'-tetrabromo-1,1'-biphenyl)-2,2'-diolato-O,O']-borate(1-);
melting point=>350° C.

EXAMPLE 16

Guanidine bis-[2,2-bis-(chloromethyl)-1,3-propanediolato]-borate(1-);
melting point=248°-249° C.

EXAMPLE 17

Diethylammonium bis-(tetrabromopyrocatecholato)-borate(1-);
melting point=>270° C. (decomposition).

EXAMPLE 18

Cyclohexylammonium bis-(tetrabromopyrocatecholato)borate(1-);
melting point=>300° (decomposition).

EXAMPLE 19 n-Hexylammonium bis-(tetrabromopyrocatecholato)-borate(1-);
melting point=248°-251° C. (decomposition).

EXAMPLE 20

Diiso-butylammonium bis-(tetrabromopyrocatecholato)borate(1-);
melting point=210°-213° C. (decomposition).

EXAMPLE 21

Dimethylphenylammonium bis-(tetrabromopyrocatecholato)-borate(1-);
melting point=243°-245° C.

EXAMPLE 22

Triethylammonium bis-[1,2,3,4,7,7-hexachloro-bicyclo(2,2,1)hept-2-ene-5,6-bis-methanolato]-borate(1-);

melting point = >350° C. (decomposition).

EXAMPLE 23

Hydrogen bis-(tetrabromopyrocatecholato)-borate(1-);
melting point = >290° C. (decomposition).

EXAMPLE 24

Hydrazine bis-[(3,3′,5,5′-tetrabromo-1,2′-biphenyl)-2,2′-diolato-O,O′]-borate(1-);
melting point = >350° C. (decomposition).

EXAMPLE 25

Triethylammonium bis-[2,2-bis-(bromomethyl)-1,3-propanediolato]-borate(1-);
melting point = ~30° C. softening.

EXAMPLE 26

Guanidine-[2,2-bis-(iodomethyl)-1,3-propanediolato-2′,2′-bis-(bromomethyl)-1′,3′-propanediolato]-borate(1-);
melting point = 214°–218° C.

EXAMPLE 27

Diethylammonium-[2,2-bis-(bromomethyl)-1,3-propanediolato-tetrabromopyrocatecholato]-borate(1-);
melting point = 269°–271° C.

EXAMPLE 28

Triethylammonium bis-[(3,3′,5,5′-tetrabromo-1,1′-biphenyl)-2,2′-diolato-O,O′]-borate(1-);
melting point = >281° C. (decomposition).

EXAMPLE 29

A mixture which contains 100 parts of a polyol with a hydroxyl number of about 500, 35 parts of trichlorofluoromethane, 1 part of N,N-dimethylcyclohexylamine, 12 parts of the compound according to Example no. 2 and 4 parts of $Sb_2O_3$ is weighed into a glass beaker. This mixture is mixed thoroughly with a propeller stirrer at 1000 rpm for about 60 seconds. 146 parts of 4,4′-diisocyanatodiphenylmethane are now introduced into this mixture and mixing is continued for about a further 10 seconds. The mixture is now poured into a paper mould. The foam obtained has a density of 39.2 g/l.

Further foams were prepared analogously using various compounds according to the invention.

The compounds employed for this, the parts by weight of the compounds employed, relative to 100 parts of polyol, the nature and amount of synergistic agents or fillers used, the foam densities and the burning properties of the foams are compared in Table 1. The flammability of the foams was investigated and classified with the aid of ASTM Test D 1692-67T. To carry out this test, test pieces having the dimensions 15.2 cm × 5.1 cm × 1.3 cm were cut out of the solid foams obtained in each case. From the values obtained, it can be seen that some of the resulting foams were self-extinguishing, but most received the classification non-flammable (according to D 1692-67T).

EXAMPLE 30

37.8 parts of epoxide resin based on bisphenol A, 25.2 parts of polyaminoimidazoline and 7 parts of the compound according to Example 1 are mixed thoroughly in a glass beaker by stirring with a basket-type stirrer (at 1000 rpm for about 120 seconds). After curing, ASTM test ASTM D-635-63 was carried out with the small hardened rods.

Further epoxide resins were manufactured analogously using various compounds according to the invention. The compounds employed for this, the particular percent by weight of the compounds employed and of the synergistic agent and the burning properties of the resin are compared in Table 2.

EXAMPLE 31

0.17 part of N,N-dimethylaniline, 2.208 parts of benzoyl peroxide paste (50% strength), 4.8 parts of the compound according to Example 1 and 1.6 parts of $Sb_2O_3$ are weighed into 71.392 parts of a commercially available, unsaturated polyester prepolymer in a glass beaker and the components are mixed thoroughly with a basket-type stirrer at 800 rpm for about 4 minutes. After curing, ASTM test ASTM D-635-63 is carried out with the test piece obtained.

Further polyester resins were manufactured analogously using various compounds according to the invention. The results are summarized in Table 3.

TABLE 1

(polyurethane foams)

| Compound According to Example No. | Parts by Weight of the compound relative to 100 parts of Polyol | $Sb_2O_3$ parts by weight | $Al(OH)_3$ parts by weight | Density of foam g/l | Time elapsed before extinction (seconds) | Extent of burning (%) | Extent of burning (cm) | Burning rate (cm/minute) | Class |
|---|---|---|---|---|---|---|---|---|---|
| 2 | 12 | 4 | — | 39.2 | 42.5 | 29.7 | 3.76 | 5.3 | n.f[1] |
| 7 | 12 | 4 | — | 40.6 | 50.0 | 31.1 | 3.95 | 4.7 | n.f |
| 18 | 12 | 4 | — | 52.6 | 62.5 | 46.3 | 5.87 | 5.64 | s.e[2] |
| 10 | 8 | 4 | — | 36.9 | 37.75 | 31.7 | 4.02 | 6.4 | n.f |
| 11 | 22 | — | — | 36.4 | 66.28 | 59.5 | 7.55 | 6.84 | s.e |
| 11 | 8 | 4 | — | 59.3 | 50.0 | 27.6 | 3.5 | 4.2 | n.f |
| 11 | 8 | 4 | 25 | 60.9 | 56.0 | 19.0 | 2.41 | 2.5 | n.f |
| 11 | 8 | 4 | 10 | 56.0 | 56.1 | 37.7 | 4.78 | 5.12 | n.f |
| 11 | 24 | 12 | 10 | 63.4 | 55.4 | 14.25 | 1.81 | 1.96 | n.f |
| 11 | 25 | — | 15 | 62.6 | 63.5 | 32.5 | 4.13 | 3.9 | s.e |
| 12 | 15 | 5 | — | 37.1 | 44.8 | 29.7 | 3.77 | 5.0 | n.f |

[1] n.f = non-flammable
[2] s.e = self-extinguishing

TABLE 2

| | | | (epoxide resins) | | | | |
|---|---|---|---|---|---|---|---|
| Compound according to Example No. | % by weight of the compound | % by weight of $Sb_2O_3$ | Time elapsed before extinction (seconds) | Extent of burning (%) | Extent of burning (cm) | Burning rate (cm/minute) | Class |
| 1 | 10 | — | 123 | 21.5 | 1.65 | 0.81 | s.e |
| 11 | 10 | 3.3 | 30 | 4.4 | 0.34 | 0.68 | s.e |
| 11 | 20 | — | 0 | 0 | 0 | 0 | n.f |
| 11 | 15 | 2.5 | 0 | 0 | 0 | 0 | n.f[1] |
| 2 | 8 | 2.6 | 57 | 6.3 | 0.48 | 0.50 | s.e[2] |
| 17 | 11 | — | 114 | 9.6 | 0.74 | 0.39 | s.e |

[1] n.f = non-flammable
[2] s.e = self-extinguishing

TABLE 3

| | | | (polyester resins) | | | | |
|---|---|---|---|---|---|---|---|
| Compound according to Example No. | % by weight of the compound | % by weight of $Sb_2O_3$ | Time elapsed before extinction (seconds) | Extent of burning (%) | Extent of burning (cm) | Burning rate (cm/minute) | Class |
| 1 | 6 | 2 | 0 | 0 | 0 | 0 | n.f[1] |
| 7 | 7 | 2 | 0 | 0 | 0 | 0 | n.f |
| 11 | 6 | 2 | 0 | 0 | 0 | 0 | n.f |
| 12 | 6 | 2 | 0 | 0 | 0 | 0 | n.f |

[1] n.f = non-flammable

What we claim is:

1. A spirocyclic boron compound of the formula

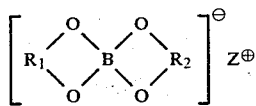  (I)

wherein $R_1$ and $R_2$, which may be the same or different, each are dihalogeno alkylene, having 2 to 6 carbon atoms, a halogen-substituted bis-methyleno-bicycloheptene-radical, tetrahalogeno-o,o'-phenylene, tetrachloro-o,o'-biphenylene, tetrabromo-o,o'-biphenylene or a group of the formula

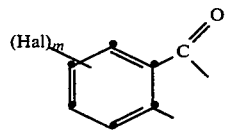  (II)

in which Hal is chlorine or bromine and m is the integer 3 or 4, and $Z^+$ is alkali metal ion, an equivalent of an alkaline earth metal, a guanidinium or hydrazinium ion or an ion of the formula

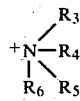

wherein $R_3$, $R_4$, $R_5$ and $R_6$, which may be the same or different, each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl.

2. A spirocyclic boron compound as claimed in claim 1 having the formula

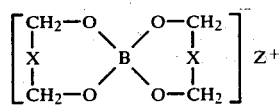  (Ia)

in which X is dihalogenoethylene or 1,3-dihalogenopropylen-2,2-, whereby halogen is selected from the group consisting of chlorine, bromine and iodine and $Z^+$ is, alkali metal ion, an equivalent of an alkaline metal earth, a guanidinium or hydrazinium ion or an ion of the formula

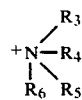

wherein $R_3$, $R_4$, $R_5$ and $R_6$, which may be the same or different each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl.

3. A spirocycic boron compound as claimed in claim 1 having the formula

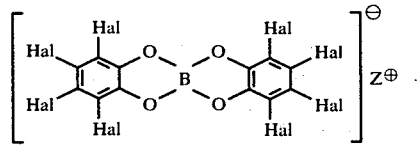  (Ib)

in which Hal is bromine or chlorine and $Z^+$ is alkali metal ion, an equivalent of, a guanidinium or hydrazinium ion or an ion of the formula

wherein $R_3$, $R_4$, $R_5$ and $R_6$, which may be the same or different each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl.

4. A spirocyclic boron compound as claimed in claim 1 of the formula

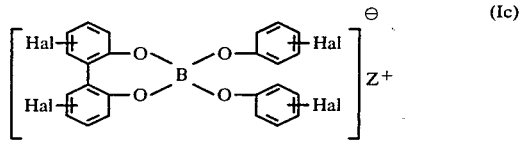

in which Hal is chlorine or bromine and $Z^+$ is alkali metal ion, an equivalent of an alkaline metal earth, a guanidinium or hydrazinium ion or an ion of the formula

wherein $R_3$, $R_4$, $R_5$ and $R_6$, which may be the same or different each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl.

5. A spirocyclic boron compound as claimed in claim 1 of the formula

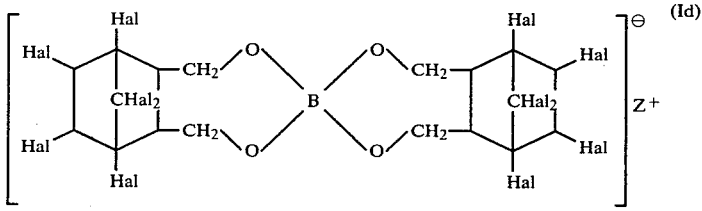

in which Hal is chlorine or bromine and $Z^+$ is alkali metal ion, an equivalent of an alkaline earth metal, a guanidinium or hydrazinium ion or an ion of the formula

wherein $R_3$, $R_4$, $R_5$ and $R_6$, which may be the same or different each are hydrogen, alkyl with 1 to 8 carbon atoms, cycloalkyl with 5 or carbon atoms or phenyl, whereby in the case where one of the radicals $R_3$, $R_4$, $R_5$ or $R_6$ is phenyl, the other ones have a meaning other than phenyl.

6. A spirocyclic compound as claimed in claim 1 of the formula

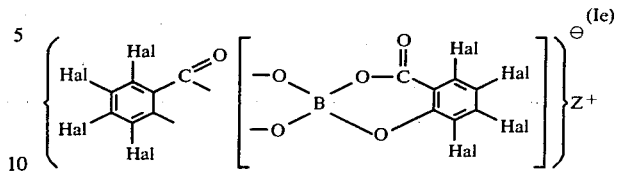

in which Hal is bromine or chlorine and $Z^+$ is alkali metal ion, an equivalent of an alkaline earth metal, a guanidinium or hydrazinium ion or an ion of the formula

wherein $R_3$, $R_4$, $R_5$ and $R_6$, which may be the same or different each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl.

7. A spirocyclic compound as claimed in claim 1 of the formula

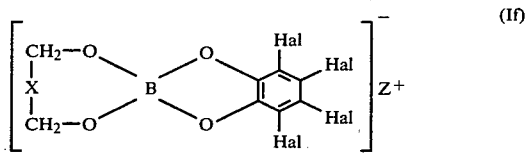

in which X is dihalogenoethylene or 1,3-dihalogenopropylene-2,2, whereby halogeno is selected from the group consisting of chlorine, bromine and iodine, Hal is bromine or chlorine and $Z^+$ is alkali metal ion, an equivalent of an alkaline earth metal, a guanidinium or hydrazinium ion or an ion of the formula

wherein $R_3$, $R_4$, $R_5$ and $R_6$, which may be the same or different each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl.

8. A compound as claimed in claim 2, said compound being a salt of Bis-[2,2-bis-(bromomethyl)-1,3-propanediolato]-borate(1-) with guanidine, sodium-hydroxide, ammonia, triethylamine or diethylamine.

9. A compound as claimed n claim 3, said compound being a salt of Bis-(tetrabromopyrocatecholato)-borate(1) with tetraethylammoniumhydroxide, triethylammoniumhydroxide, diethylammoniumhydroxide, diisobutylammonium hydroxide, ammoniumhydroxide, sodium hydroxide, cyclohexylammonium hydroxide, n-hexylammoniumhydroxide or dimethylphenylammoniumhydroxide.

10. A compound according to claim 2, said compound being guanidine bis-(2,3-dibromo-1,4-butanediolato)-borate(1-)

11. A compound according to claim 2, said compound being sodium bis-[2,2-bis-(bromomethyl)-1,3-propanediolato]-borate(1-)

12. A compound according to claim 3, said compound being triethylammonium bis-(tetrabromopyrocatecholato)-borate(1-)

13. A compound according to claim 3, said compound being diethylammonium bis-(tetrabromopyrocatecholato)-borate(1-)

14. A compound according to claim 4, said compound being guanidine bis-[(3,3',5,5'-tetrabromo-1,1'-biphenyl)-2,2'-diolato-O,O']-borate(1-)

15. A compound according to claim 5, said compound being triethylammonium bis-[1,2,3,4,7,7-hexachloro-bicyclo(2,2,1)hept-2-ene-5,6-bis-methanolato]-borate(1-)

16. A flame retarding agent which comprises a spirocyclic boron compound of the formula

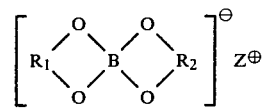

wherein $R_1$ and $R_2$, which may be the same or different, each are dihalogeno alkylene, having 2 to 6 carbon atoms, a halogen-substituted bis-methyleno-bicycloheptene-radical, tetrahalogeno-o,o'-phenylene, tetrachloro-o,o'-biphenylene, tetrabromo-o,o'-biphenylene or a group of the formula

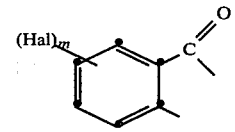

in which Hal is chlorine or bromine and m is the integer 3 or 4, and $Z^+$ is alkali metal ion, an equivalent of an alkaline earth metal, a guanidinium or hydrazinium ion or an ion of the formula

wherein $R_3$, $R_4$, $R_5$ and $R_6$, which may be the same or different, each are hydrogen, alkyl with 1 to 8 carbon atoms, cycloalkyl with 5 or 6 carbon atoms or phenyl, whereby in the case where one of the radicals $R_3$, $R_4$, $R_5$ or $R_6$ is phenyl, the other ones have a meaning other than phenyl and $Sb_2O_3$ as synergistic agent.

* * * * *